US012682608B2

(12) United States Patent
He

(10) Patent No.: US 12,682,608 B2
(45) Date of Patent: Jul. 14, 2026

(54) METHOD AND SYSTEM FOR CLASSIFYING BREAST ULTRASOUND IMAGE, ELECTRONIC DEVICE AND MEDIUM

(71) Applicant: TenD.AI Medical Technology (Shanghai) Co., Ltd., Shanghai (CN)

(72) Inventor: Minliang He, Shanghai (CN)

(73) Assignee: TenD.AI Medical Technology (Shanghai) Co., Ltd., Shanghai (CN)

( * ) Notice: Subject to any disclaimer, the term of this patent is extended or adjusted under 35 U.S.C. 154(b) by 233 days.

(21) Appl. No.: 18/763,442

(22) Filed: Jul. 3, 2024

(65) Prior Publication Data

US 2025/0157191 A1 May 15, 2025

(30) Foreign Application Priority Data

Nov. 9, 2023 (CN) .......................... 202311490395.3

(51) Int. Cl.
*G06V 10/764* (2022.01)
*A61B 8/08* (2006.01)
(Continued)

(52) U.S. Cl.
CPC .......... *G06V 10/764* (2022.01); *G06V 10/774* (2022.01); *G06V 10/82* (2022.01); *A61B 8/0825* (2013.01); *G06V 2201/03* (2022.01)

(58) Field of Classification Search
CPC ................ A61B 8/0825; A61B 8/0833; G06T 2207/10132; G06T 2207/20081; G06T 2207/20084; G06T 2207/30068; G06V 10/44; G06V 10/764; G06V 10/774; G06V 10/806; G06V 10/82; G06V 2201/03
See application file for complete search history.

(56) References Cited

U.S. PATENT DOCUMENTS

2012/0208161 A1* 8/2012 Takata ................... G16H 40/20
434/262
2023/0414204 A1* 12/2023 Koshino ................ A61B 8/085

FOREIGN PATENT DOCUMENTS

CN      110728674 A  *  1/2020  .......... G06T 7/0012
CN      111243730 A  *  6/2020  .......... G16H 15/00
(Continued)

OTHER PUBLICATIONS

Wang et al. "Deep transfer learning radiomics based on two-dimensional ultrasound for predicting the efficacy of neoadjuvant chemotherapy in breast cancer." (2023). (Year: 2023).*
(Continued)

*Primary Examiner* — Katrina R Fujita
(74) *Attorney, Agent, or Firm* — Jacob M. Ward; Ward Law Office LLC

(57) ABSTRACT

A method and a system for classifying a breast ultrasound image, an electronic device and a medium are provided, which relates to the field of image processing. The method includes: acquiring a breast ultrasound image to be classified; inputting the breast ultrasound image to be classified into an image classification model to obtain a final classification result; where the final classification result is that a posterior echo is enhanced, the posterior echo is unchanged, the posterior echo is attenuated-sharp or the posterior echo is attenuated-blurred. The present disclosure can improve the accuracy and efficiency of classifying a breast ultrasound image.

19 Claims, 7 Drawing Sheets

(51) Int. Cl.
    *G06V 10/774*        (2022.01)
    *G06V 10/82*         (2022.01)

(56)                References Cited

FOREIGN PATENT DOCUMENTS

| CN | 112489788 | A | * | 3/2021 | ............. | G06N 3/045 |
| CN | 114170241 | A | * | 3/2022 | ......... | G06F 18/2415 |
| CN | 114202514 | A | * | 3/2022 | ........... | G06F 18/241 |
| CN | 114757953 | A | * | 7/2022 | ............. | G06F 18/24 |
| CN | 117809333 | A | * | 4/2024 | ............... | G06N 3/08 |

OTHER PUBLICATIONS

Chinese Office Action for Application No. CN202311490395.3 dated Apr. 29, 2024.

* cited by examiner

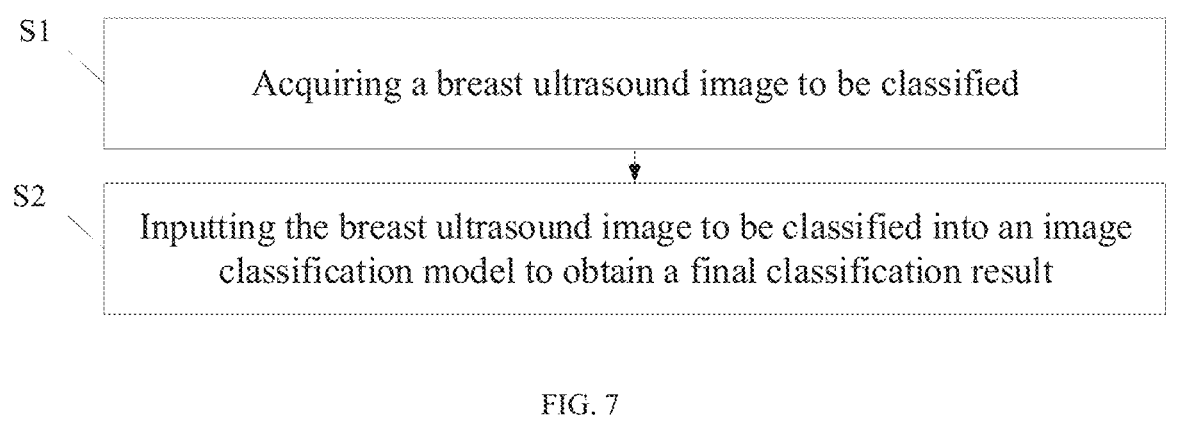

S1

Acquiring a breast ultrasound image to be classified

S2

Inputting the breast ultrasound image to be classified into an image classification model to obtain a final classification result

FIG. 7

METHOD AND SYSTEM FOR CLASSIFYING BREAST ULTRASOUND IMAGE, ELECTRONIC DEVICE AND MEDIUM

CROSS-REFERENCE TO RELATED APPLICATION

This patent application claims the benefit and priority of Chinese Patent Application No. 202311490395.3 filed with the China National Intellectual Property Administration on Nov. 9, 2023, the disclosure of which is incorporated by reference herein in its entirety as part of the present application.

TECHNICAL FIELD

The present disclosure relates to the field of image processing, in particular to a method and a system for classifying a breast ultrasound image, an electronic device and a medium.

BACKGROUND

Fast and accurate positioning of breast nodules is the key to breast ultrasound imaging examination. Ultrasonic doctors can judge the nature and development expectation of nodules according to the ultrasound images of nodule sections, and make corresponding diagnosis and treatment plans.

A posterior echo is one of the important indicators in the ultrasonic features of breast nodules, which is often used to evaluate benign nodules and malignant nodules. The posterior echo usually refers to the acoustic echogenic appearance below the nodules. A nodule texture is different, and the attenuation degree of the acoustic signal when penetrating through the nodule region is also different. A dense nodule region will produce greater attenuation of acoustic waves. The attenuation signs of echoes are formed below the nodule region, which may indicate malignancy. It is not easy for the nodule region with a transparent texture to attenuate, and enhancement signs of echoes may be formed below the nodule region, which may indicate benign.

However, due to the limited resolution and inherent speckle noise of the ultrasound image itself, it is difficult to sensitively capture the changes of the posterior echo signs through naked eye observation, and it is often influenced by subjective tendency. There is an urgent need for a method for classifying a breast ultrasound image to improve the accuracy and efficiency of classifying a breast ultrasound image.

SUMMARY

The present disclosure aims to provide a method and a system for classifying a breast ultrasound image, an electronic device and a medium, which can improve the accuracy and efficiency for classifying a breast ultrasound image.

In order to achieve the above objectives, the present disclosure provides the following scheme.

A method for classifying a breast ultrasound image is provided, where the method includes acquiring a breast ultrasound image to be classified; inputting the breast ultrasound image to be classified into an image classification model to obtain a final classification result; where the final classification result is that a posterior echo is enhanced, the posterior echo is unchanged, the posterior echo is attenuated-sharp or the posterior echo is attenuated-blurred; the image classification model includes a primary classification network and a secondary classification network; the primary classification network is acquired by applying a primary training set to train a primary network; the secondary classification network is acquired by applying a secondary training set to train a secondary network; the primary network and the secondary network are both deep neural networks; the primary training set includes a breast ultrasound image and a corresponding primary classification result; the corresponding primary classification result is that the posterior echo is enhanced, the posterior echo is unchanged or the posterior echo is attenuated; the secondary training set includes a breast ultrasound image in which the primary classification result is that the posterior echo is attenuated and a corresponding secondary classification result; the secondary classification result is that the posterior echo is attenuated-sharp or the posterior echo is attenuated-blurred; the breast ultrasound image to be classified is input into the primary classification network to obtain the primary classification result; when the primary classification result is that the posterior echo is enhanced or the posterior echo is unchanged, the primary classification result is the final classification result; when the primary classification result is that the posterior echo is attenuated, the breast ultrasound image to be classified is input into the secondary classification network to obtain the secondary classification result, and the secondary classification result is deemed as the final classification result.

In some embodiments, a construction process of the image classification model specifically includes: acquiring a plurality of original breast ultrasound images and a region of interest of each original breast ultrasound image; where the plurality of original breast ultrasound images include a posterior echo enhanced image, a posterior echo unchanged image, a posterior echo attenuated-sharp image and a posterior echo attenuated-unsharp image; determining a circumscribed matrix of the region of interest of each original breast ultrasound image, and determining a posterior echo prediction region according to the circumscribed matrix to obtain a labeled breast ultrasound image; preprocessing the labeled breast ultrasound image to obtain a preprocessed breast ultrasound image; the preprocessing at least includes two operations of flip transformation, random cropping, color dithering, translation transformation, scale transformation, contrast transformation, noise disturbance and rotation transformation; with the preprocessed breast ultrasound image as an input and the primary classification result as an output, training the primary network to obtain the primary classification network; with the classified breast ultrasound image as an input and the secondary classification result as an output, training the secondary network to obtain the secondary classification network; where the classified breast ultrasound image is an intermediate breast ultrasound image corresponding to the primary classification result that the posterior echo is attenuated; and the intermediate breast ultrasound image is the preprocessed breast ultrasound image.

In some embodiments, the labeled breast ultrasound image is preprocessed, and prior to the preprocessing, the method further includes: scaling the labeled breast ultrasound image to a predetermined pixel by applying an interpolation algorithm.

In some embodiments, the interpolation algorithm is Lanczos interpolation algorithm.

In some embodiments, a structure of the primary network includes an input layer, a Conv1 layer, a Fused-MBConv1, a first Fused-MBConv4, a second Fused-MBConv4, an MBConv4, a first MBConv6, a second MBConv6, a Conv2 layer, a GAP layer and a Softmax; the input layer is connected with the Conv1 layer; the Conv1 layer is connected with the Fused-MBConv1; the Fused-MBConv1 is connected with the first Fused-MBConv4; the first Fused-MBConv4 is connected with the second Fused-MBConv4; the second Fused-MBConv4 is connected with the MBConV4; the MBConv4 is connected with the first MBConv6; the first MBConv6 is connected with the second MBConv6; the second MBConv6 is connected with the Conv2 layer; the Conv2 layer is connected with the GAP layer; and the GAP layer is connected with the Softmax.

In some embodiments, a structure of the secondary network includes an input layer, a Conv1 layer, an MBConv1, a first MBConv6, a second MBConv6, a third MBConv6, a fourth MBConv6, a fifth MBConv6, a sixth MBConv6, a Conv2 layer, a GAP layer and a Sigmoid; the input layer is connected with the Conv1 layer; the Conv1 layer is connected with MBConv1; the MBConv1 is connected with the first MBConv6; the first MBConv6 is connected with the second MBConv6; the second MBConv6 is connected with the third MBConv6; the third MBConv6 is connected with the fourth MBConv6; the fourth MBConv6 is connected with the fifth MBConv6; the fifth MBConv6 is connected with the sixth MBConv6; the sixth MBConv6 is connected with the Conv2 layer; the Conv2 layer is connected with the GAP layer; and the GAP layer is connected with the Sigmoid.

A system for classifying a breast ultrasound image is provided, which is applied to the abovementioned method for classifying the breast ultrasound image, where the system includes: an acquiring module, configured to acquire a breast ultrasound image to be classified; a classifying module, configured to input the breast ultrasound image to be classified into an image classification model to obtain a final classification result; where the final classification result is that a posterior echo is enhanced, the posterior echo is unchanged, the posterior echo is attenuated-sharp or the posterior echo is attenuated-blurred; the image classification model includes a primary classification network and a secondary classification network; the primary classification network is acquired by applying a primary training set to train a primary network; the secondary classification network is acquired by applying a secondary training set to train a secondary network; the primary network and the secondary network are both deep neural networks; the primary training set includes a breast ultrasound image and a corresponding primary classification result; the corresponding primary classification result is that the posterior echo is enhanced, the posterior echo is unchanged or the posterior echo is attenuated; the secondary training set includes a breast ultrasound image in which the primary classification result is that the posterior echo is attenuated and a corresponding secondary classification result; the secondary classification result is that the posterior echo is attenuated-sharp or the posterior echo is attenuated-blurred; the breast ultrasound image to be classified is input into the primary classification network to obtain the primary classification result; when the primary classification result is that the posterior echo is enhanced or the posterior echo is unchanged, the primary classification result is the final classification result; when the primary classification result is that the posterior echo is attenuated, the breast ultrasound image to be classified is input into the secondary classification network to obtain the secondary classification result, and the secondary classification result is deemed as the final classification result.

An electronic device is provided, which includes a memory and a processor, where the memory is configured to store a computer program, and the processor runs the computer program to cause the electronic device to perform the method for classifying the breast ultrasound image described above.

A non-transitory computer-readable storage medium is provided, in which a computer program is stored, where the computer program, when executed by a processor, implements the method for classifying the breast ultrasound image described above.

According to the specific embodiment provided by the present disclosure, the present disclosure provides the following technical effects.

In the present disclosure, an image classification model is used to classify the breast ultrasound image to be classified, and the acquired final classification result is that a posterior echo is enhanced, the posterior echo is unchanged, the posterior echo is attenuated-sharp or the posterior echo is attenuated-blurred; the image classification model includes a primary classification network and a secondary classification network; the breast ultrasound image to be classified is input into the primary classification network to obtain the primary classification result; when the primary classification result is that the posterior echo is enhanced or the posterior echo is unchanged, the primary classification result is the final classification result; when the primary classification result is that the posterior echo is attenuated, the breast ultrasound image to be classified is input into the secondary classification network to obtain the secondary classification result, and the secondary classification result is deemed as the final classification result. According to the present disclosure, the final classification result is directly acquired through the image classification model, so that the efficiency of classifying a breast ultrasound image is improved, and the accuracy of classifying a breast ultrasound image is improved by using the structure of the primary classification network and the secondary classification network.

BRIEF DESCRIPTION OF THE DRAWINGS

In order to explain the embodiments of the present disclosure or the technical schemes in the prior art more clearly, the drawings that need to be used in the embodiments will be briefly introduced below. Apparently, the drawings in the following description are only some embodiments of the present disclosure. For those skilled in the art, other drawings can be acquired according to these drawings without creative labor.

FIG. 1A-FIG. 1D are pictures of an ultrasonic posterior echo according to the present disclosure, in which FIG. 1A is a picture in which a posterior echo is enhanced, FIG. 1B is a picture in which the posterior echo is unchanged, FIG. 1C is a picture in which the posterior echo is attenuated-unsharp, and FIG. 1D is a picture in which the posterior echo is attenuated-sharp.

FIG. 7 is a flowchart of a method for classifying a breast ultrasound image according to the present disclosure.

DETAILED DESCRIPTION OF THE EMBODIMENTS

The technical schemes in the embodiments of the present disclosure will be clearly and completely described with reference to the drawings in the embodiments of the present disclosure hereinafter. Apparently, the described embodiments are only some embodiments of the present disclosure, rather than all of the embodiments. Based on the embodiments of the present disclosure, all other embodiments acquired by those ordinarily skilled in the art without creative labor fall within the scope of protection of the present disclosure.

The purpose of the present disclosure is to provide a method and a system for classifying a breast ultrasound image, an electronic device and a medium, which can improve the accuracy and efficiency of classifying a breast ultrasound image.

In order to make the above objects, features and advantages of the present disclosure more obvious and understandable, the present disclosure will be explained in further detail below with reference to the drawings and specific embodiments.

Embodiment 1

Figure 2:
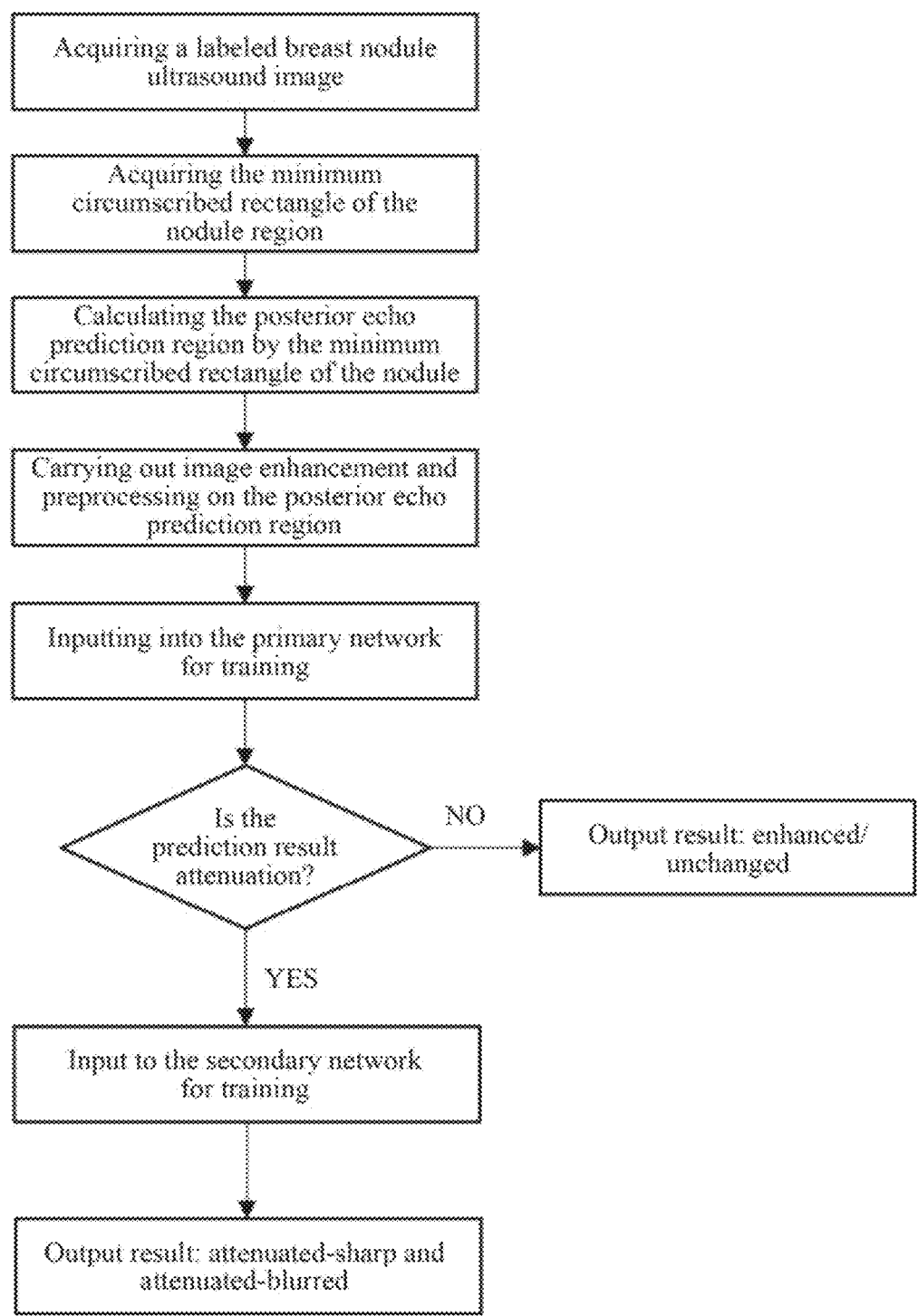
FIG. 2 is a flow chart of an ultrasonic detection method of the posterior echo of a breast nodule according to the present disclosure in practical application.

As shown in FIG. 2 and FIG. 7, the present disclosure provides a method for classifying a breast ultrasound image, where the method includes the following steps S1 to S2.

In Step S1: a breast ultrasound image to be classified is acquired;

In Step S2: the breast ultrasound image to be classified is input into an image classification model to obtain a final classification result. The final classification result is that a posterior echo is enhanced, the posterior echo is unchanged, the posterior echo is attenuated-sharp or the posterior echo is attenuated-blurred, and the image classification model includes a primary classification network and a secondary classification network. The primary classification network is acquired by applying a primary training set to train a primary network, and the secondary classification network is acquired by applying a secondary training set to train a secondary network. The primary network and the secondary network are both deep neural networks, the primary training set includes a breast ultrasound image and a corresponding primary classification result; the corresponding primary classification result is that the posterior echo is enhanced, the posterior echo is unchanged or the posterior echo is attenuated. The secondary training set includes a breast ultrasound image in which the primary classification result is that the posterior echo is attenuated and a corresponding secondary classification result, and the secondary classification result is that the posterior echo is attenuated-sharp or the posterior echo is attenuated-blurred. The breast ultrasound image to be classified is input into the primary classification network to obtain the primary classification result, and when the primary classification result is that the posterior echo is enhanced or the posterior echo is unchanged, the primary classification result is the final classification result; when the primary classification result is that the posterior echo is attenuated, the breast ultrasound image to be classified is input into the secondary classification network to obtain the secondary classification result, and the secondary classification result is deemed as the final classification result.

Further, the primary network is BrEff1-net. The secondary network is BrEff2-net.

As a specific embodiment, the construction process of the image classification model specifically includes the following steps.

In Step S101, a plurality of original breast ultrasound images and a region of interest of each original breast ultrasound image are acquired; where the plurality of original breast ultrasound images include a posterior echo enhanced image, a posterior echo unchanged image, a posterior echo attenuated-sharp image and a posterior echo attenuated-unsharp image.

Figure 1A:
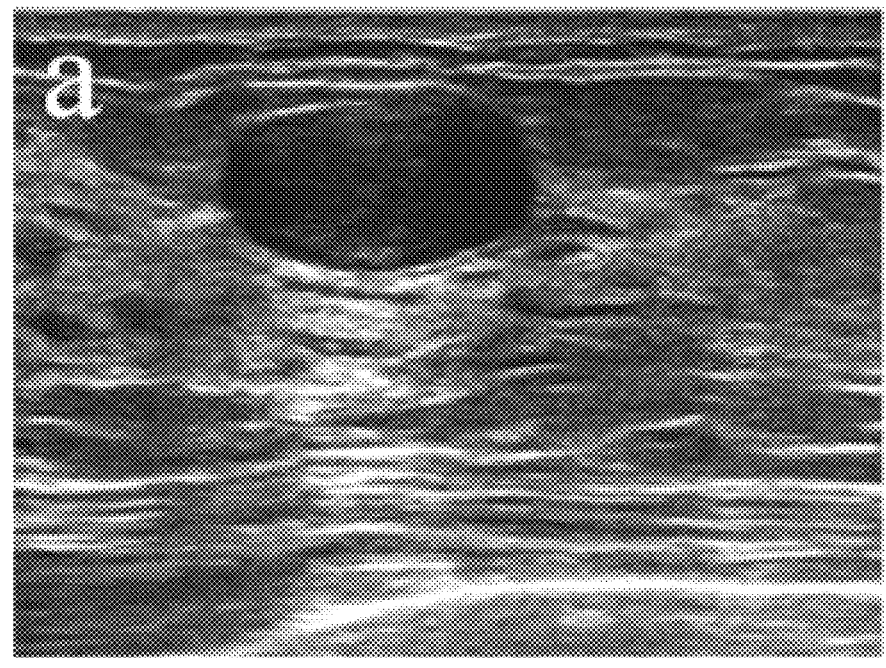
Figure 1B:
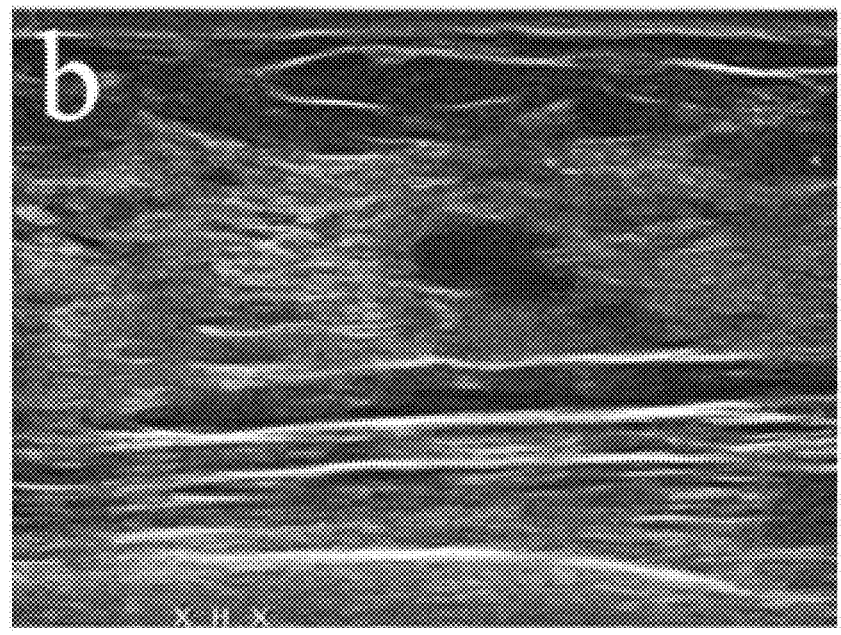
Figure 1C:
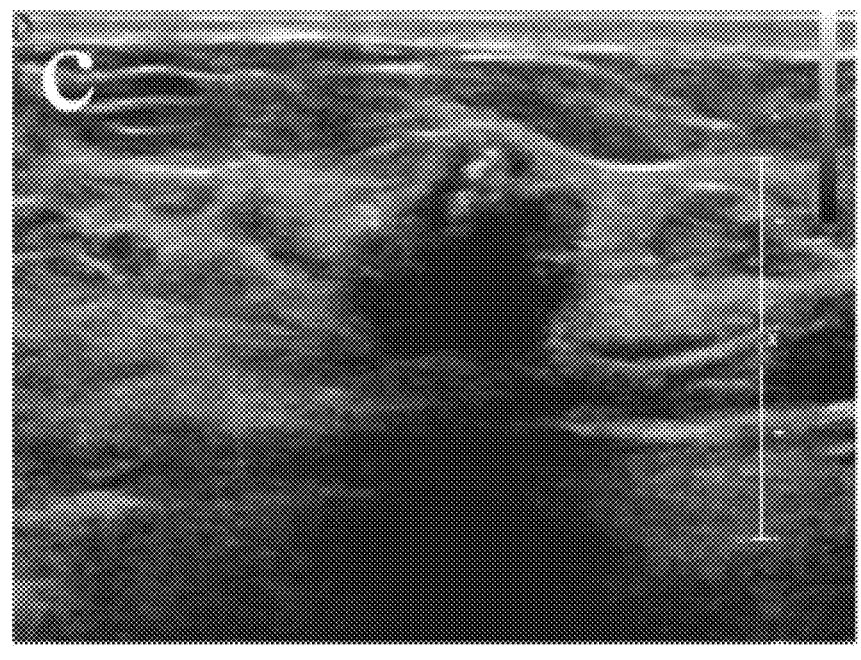
Figure 1D:
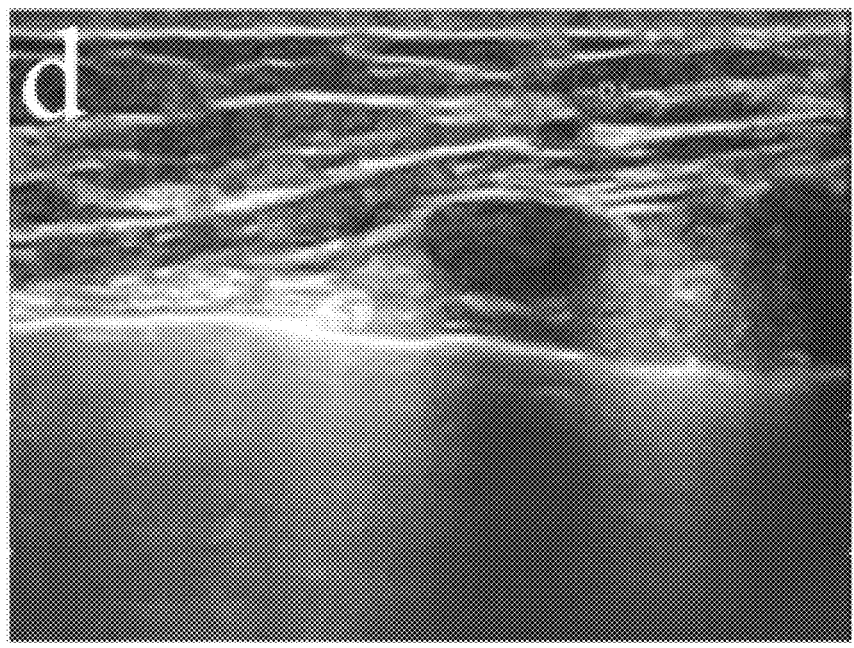

In practical application, as shown in FIG. 1A-FIG. 1D. First, a breast ultrasound image containing a breast nodule is acquired. FIG. 1A is a picture in which a posterior echo is enhanced, FIG. 1B is a picture in which a posterior echo is unchanged, FIG. 1C is a picture in which a posterior echo is attenuated-unsharp, and FIG. 1D is a picture in which a posterior echo is attenuated-sharp. A total of 2561 breast ultrasound images containing breast nodules are used in the present disclosure, where 602 images are posterior echo enhanced images, 1760 images are posterior echo unchanged images, 106 images are posterior echo attenuated-sharp images, and 93 images are posterior echo attenuated-unsharp images.

The boundary contour of nodules is marked by a professional sonographer by points. Any nodule P contains a total of no less than ten outline points, and the edge outline of the nodule formed by connecting these points is denoted as the region of interest of the image. The set of all outline points is $(x_i, y_i) \in P$, $(i \geq 10)$.

In Step S102: a circumscribed matrix of the region of interest of each original breast ultrasound image is determined, and a posterior echo prediction region is determined according to the circumscribed matrix to obtain a labeled breast ultrasound image. The labeled breast ultrasound image is the image of the posterior echo prediction region.

In Step S103: the labeled breast ultrasound image is scaled to a predetermined pixel by applying an interpolation algorithm. Specifically, the interpolation algorithm is Lanczos interpolation algorithm.

In practical application, first, the minimum circumscribed rectangular region $Rect_{ROI}$ of the nodule is taken to satisfy:

$$Rect_{ROI}(x, y, w, h) = \begin{cases} x = \min(P_x) \\ y = \min(P_y) \\ w = \max(P_x) - \min(P_x) \\ h = \max(P_y) - \min(P_y) \end{cases}$$

where $Rect_{ROI}(x,y,w,h)$ is the circumscribed rectangle of the nodule in the image, x and y are the horizontal and vertical coordinates of the upper left corner of the circumscribed rectangle, w and h are the width and height of the circumscribed rectangle, $P_x$ is the set of horizontal coordinates of all outline points, and $P_y$ is the set of vertical coordinates of all outline points. The minimum circumscribed rectangular region $Rect_{ROI}$ corresponds to the region 1 in FIG. 3.

After obtaining the minimum circumscribed rectangle of the region of interest, the posterior echo region $Rect_{back}$ is acquired, and its calculation formula is as follows:

$$Rect_{back}(x, y, w, h) = \begin{cases} x = \min(P_x) + w/8 \\ y = \min(P_y) + (9/8)h \\ w = (3/4)(\max(P_x) - \min(P_x)) \\ h = \max(P_y) - \min(P_y) \end{cases}$$

Figure 3:
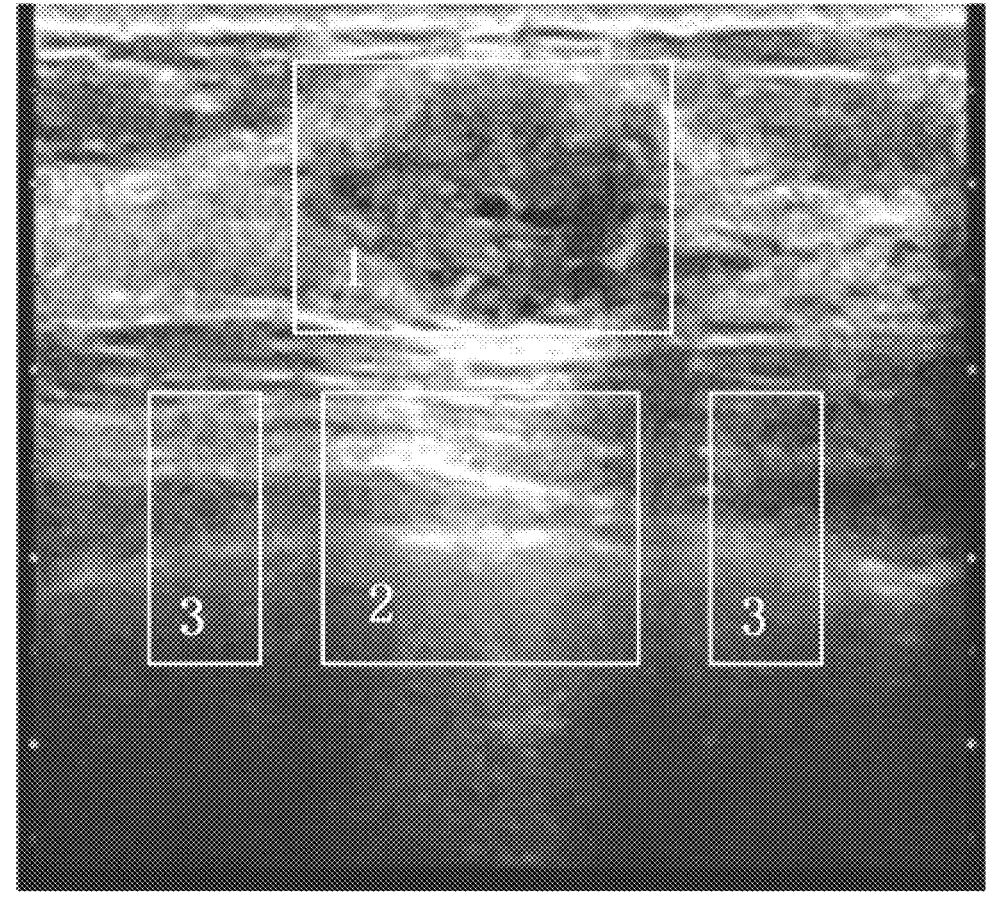
FIG. 3 is a picture of the posterior echo and a reference region outlined with rectangles according to the present disclosure.

The posterior echo region $Rect_{back}$ corresponds to the region 2 in FIG. 3.

The calculation formulas of the posterior echo reference regions $Rect_{c1}$ and $Rect_{c2}$ are as follows:

$$Rect_{c1}(x, y, w, h) = \begin{cases} x = \min(P_x) - (3/8)w \\ y = \min(P_y) + (9/8)h \\ w = (1/4)(\max(P_x) - \min(P_x)) \\ h = \max(P_y) - \min(P_y) \end{cases}$$

$$Rect_{c2}(x, y, w, h) = \begin{cases} x = \min(P_x) + w/8 \\ y = \min(P_y) + (9/8)h \\ w = (1/4)(\max(P_x) - \min(P_x)) \\ h = \max(P_y) - \min(P_y) \end{cases}$$

The posterior echo reference regions $Rect_{c1}$ and $Rect_{c2}$ correspond to the region 3 in FIG. 3.

Figure 4:
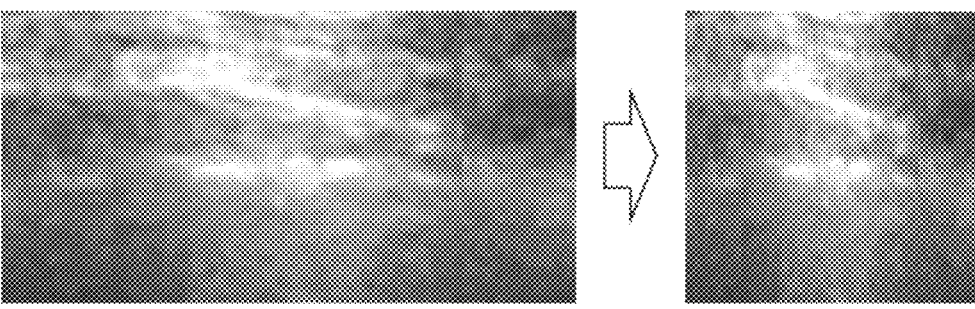
FIG. 4 is a picture of a posterior echo prediction region according to the present disclosure.

The construction steps of the posterior echo prediction region are as follows: first, three images of the posterior echo region and the posterior echo reference regions are intercepted from the original image according to the above formula. Thereafter, the three images are stitched into one image in an order that the posterior echo region is in the middle and the posterior echo reference regions are on both sides, so as to obtain the posterior echo prediction region. Finally, the stitched images are uniformly scaled to 224×224 pixels by using the Lanczos interpolation algorithm, as shown in FIG. 4.

In Step S104: on the basis of Step S103, the labeled breast ultrasound image are preprocessed to obtain a preprocessed breast ultrasound image; the preprocessing at least includes two operations of flip transformation, random cropping, color dithering, translation transformation, scale transformation, contrast transform, noise disturbance and rotation transformation.

In practical application, in order to enrich the image training set, extract the image features better and prevent the model from over-fitting before deep learning network training, two or four methods are randomly selected from the following eight image enhancement methods to enhance the image during the training.

1. Flip transformation, in which the image is flipped horizontally or vertically.

2. Random cropping, in which the region of the image with a ratio of 0.6 to 1.0 is cropped randomly.

3. Color dithering, in which the principal component analysis is carried out in each RGB color channel of the pixel value of the training set to obtain three principal direction vectors in the RGB space, and the most important principal component (feature vector) is selectively retained to generate new image samples with changed colors.

4. Translation transformation, in which the image is randomly moved by 0-20 pixels in one of the four directions of up, down, left and right, and the redundant part is supplemented by 0-intensity pixels.

5. Scale transformation, in which the image is enlarged or reduced according to the specified scale; or the specified scale size is used to filter the image to construct a scale space, change the size or fuzzy degree of the image content, and finally change the image resolution to multiples of the original image, such as 0.8, 0.9, 1.1, 1.2, as a new image.

6. Contrast transform, in which first, the input image to be processed is acquired. the average gray value of the image is calculated for subsequent processing. The contrast of the image is transformed, and the contrast of the image is enhanced by adjusting the brightness value and distribution of the image pixels. According to the preset contrast enhancement parameters, the contrast of the image is adjusted to obtain different contrast enhancement effects.

7. Noise disturbance, in which an original image is received as input to generate a salt and pepper noise image with the same size as the original image. A Gaussian noise image with the same size as the original image is generated. The generated noise image is fused with the original image, and the fused image is output as the disturbed image. The fused image has increased randomness and complexity, and retains the main features of the original image. The robustness and the saturation of the image processing algorithm can be improved by processing the disturbed image.

8. Rotation transformation, in which the image is randomly rotated by 0 to 15 degrees clockwise or counterclockwise, and the redundant part is supplemented by 0-intensity pixels.

In Step S105: with the preprocessed breast ultrasound image as an input and the primary classification result as an output, the primary network is trained to obtain the primary classification network.

In Step S106: with the classified breast ultrasound image as an input and the secondary classification result as an output, the secondary network is trained to obtain the secondary classification network; where the classified breast ultrasound image is an intermediate breast ultrasound image corresponding to the primary classification result that the posterior echo is attenuated; and the intermediate breast ultrasound image is the preprocessed breast ultrasound image.

Figure 5:
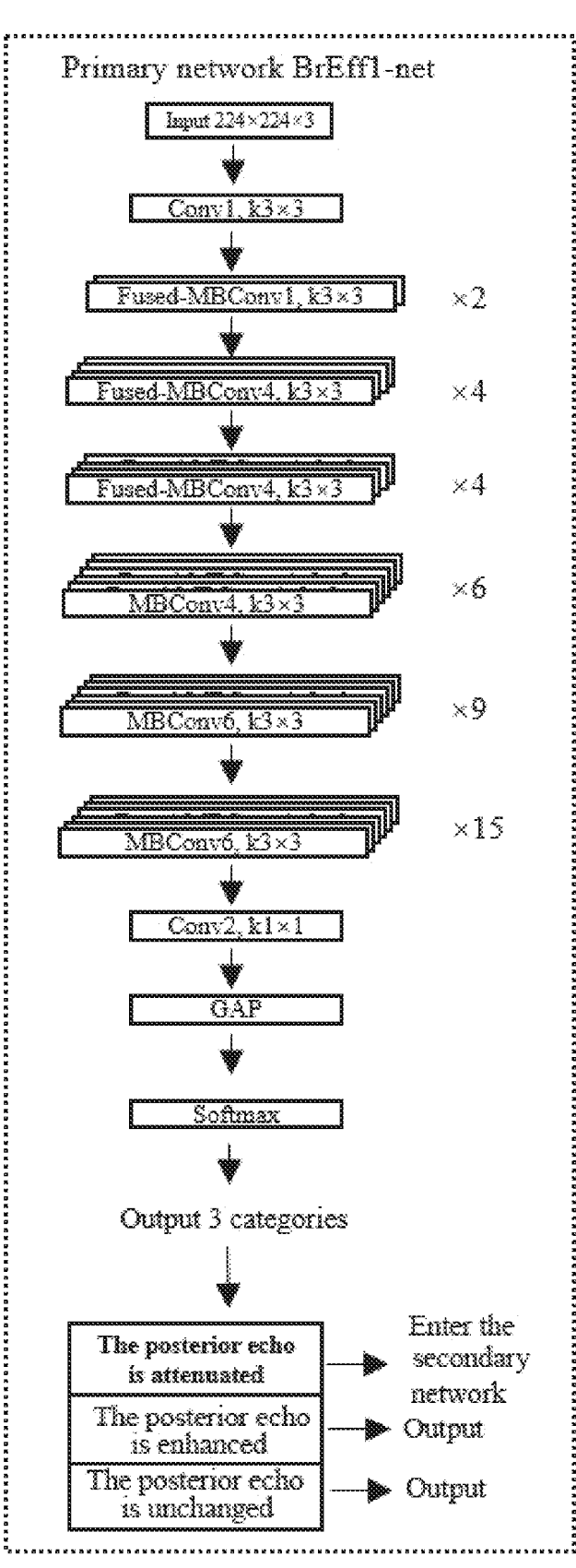
FIG. 5 is a schematic diagram of a primary network structure according to the present disclosure.
Figure 6:
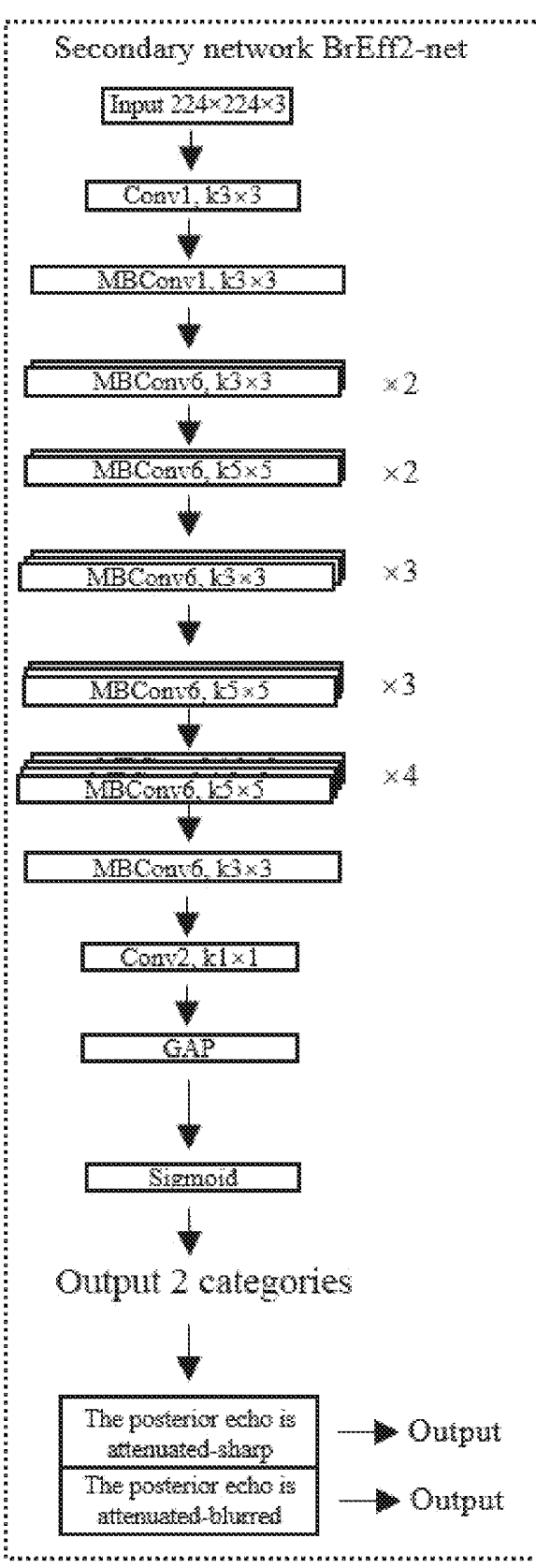
FIG. 6 is a schematic diagram of a secondary network structure according to the present disclosure.

In practical application, a two-level network is constructed in the present disclosure to classify the posterior echo of the breast. The two-level network is shown in FIGS. 5 and 6. The primary network is BrEff1-net, and the secondary network is BrEff2-net. During training, inputs of the primary network and the secondary network are the images of which the posterior echo prediction region is processed in Step 103 and Step 104. BrEff1-net is BreastEfficientStage1Net, which is improved based on the existing network EfficientNetv2s. BrEff2-net is BreastEfficientStage2Net, which is improved based on the existing network EfficientNetb0.

In the present disclosure, first, the input images are classified into three categories by using BrEff1-net as the deep neural network: those with the posterior echo being enhanced, those with the posterior echo being attenuated, and those with the posterior echo being unchanged. The primary network uses the EfficientNetV2-s framework as the basic skeleton.

BrEff1-net contains an input layer with the input size of (w, h, c), where w=224, h=224, and c=3. The input layer is connected to the skeleton network EfficientNetV2-s, which consists of a series of repeated MBConv-Blocks and Fused-MBConv-Block. The MBConv module is the core module in EfficientNet series, which mainly consists of a series of depthwise separable convolution modules, extended convolution modules and Squeeze-and-Exclusion (SE) modules for extracting image features at different levels. Fused-MBConv-Block combines the two operations of Depthwise Separable Convolution and Squeeze-and-Excitation to improve the efficiency and performance of the network. After all convolution layers, the convolution output is expanded by using a global average pooling layer, and then is connected to a dropout layer with 0.5 removal probability, and is finally connected to the output layer using the SoftMax activation function. The middle layer uses leaky ReLU as the activation function. Adam optimizer is used for parameter back propagation in the training process. The output results are classified into three categories, namely, the posterior echo is enhanced, the posterior echo is attenuated, and the posterior echo is unchanged. If the output of the primary network is that the posterior echo is enhanced and the posterior echo is unchanged, the output is the final output result. If the output of the primary network is that the posterior echo is attenuated, the input original image is input into the secondary network for further judgment.

Specifically, the structure of the primary network includes an input layer, a Conv1 layer, a Fused-MBConv1, a first Fused-MBConv4, a second Fused-MBConv4, an MBConv4, a first MBConv6, a second MBConv6, a Conv2 layer, a GAP layer and a Softmax.

The input layer is connected with the Conv1 layer; the Conv1 layer is connected with the Fused-MBConv1; the Fused-MBConv1 is connected with the first Fused-MB-Conv4; the first Fused-MBConv4 is connected with the second Fused-MBConv4; the second Fused-MBConv4 is connected with the MBConV4; the MBConv4 is connected with the first MBConv6; the first MBConv6 is connected with the second MBConv6; the second MBConv6 is connected with the Conv2 layer; the Conv2 layer is connected with the GAP layer; and the GAP layer is connected with the Softmax.

Further, BrEff1-net contains an input layer with the input size of (w, h, c), where w=224, h=224, and c=3. The input layer is connected with one Conv1 layer with the size of K3×3. Thereafter, the Conv1 layer is connected with two layers of Fused-MBConv1 with the size of K3×3. Subsequently, the two layers of Fused-MBConv1 are connected with four layers of Fused-MBConv4 with the size of K3×3. Thereafter, the four layers of Fused-MBConv4 are connected with the four layers of Fused-MBConv4 with the size of K3×3. Thereafter, the four layers of Fused-MBConv4 are connected with six layers of MBConv4 with the size of K3×3. The six layers of MBConv4 are connected with the nine layers of MBConv6 with the size of K3×3. Thereafter, the nine layers of MBConv6 are connected with fifteen layers of MBConv6 with the size of K3×3. Thereafter, the fifteen layers of MBConv6 are connected with one Conv2 layer with the size of K1×1. Thereafter, the one Conv2 layer is connected with the GAP layer. Thereafter, the GAP layer is connected with the Softmax.

In the present disclosure, BrEff2-net is used as the secondary network. The images with the classification result in which the posterior echo is attenuated are further classified into two subcategories: those with the posterior echo being attenuated-sharp and those with the posterior echo being attenuated-blurred.

The secondary network uses the EfficientNet-b0 framework as the basic skeleton. BrEff2-net contains an input layer with the input size of (w, h, c), where w=224, h=224, and c=3. The input layer is connected to the skeleton network EfficientNetV2-b0, which also consists of a series of repeated Blocks. Each Block consists of a plurality of MBConv modules and a convolution layer. After all convolution layers, the convolution output is expanded by using a global average pooling layer, and then is connected to a dropout layer with 0.5 removal probability, and is finally connected to the output layer using the sigmoid activation function. The middle layer uses leaky ReLU as the activation function. Adam optimizer is used for parameter back propagation in the training process. The output results are classified into two categories, namely, those with the posterior echo being attenuated-sharp and those with the posterior echo being attenuated-blurred.

Specifically, the structure of the secondary network includes an input layer, a Conv1 layer, an MBConv1, a first MBConv6, a second MBConv6, a third MBConv6, a fourth MBConv6, a fifth MBConv6, a sixth MBConv6, a Conv2 layer, a GAP layer and a Sigmoid.

The input layer is connected with the Conv1 layer; the Conv1 layer is connected with MBConv1; the MBConv1 is connected with the first MBConv6; the first MBConv6 is connected with the second MBConv6; the second MBConv6 is connected with the third MBConv6; the third MBConv6 is connected with the fourth MBConv6; the fourth MBConv6 is connected with the fifth MBConv6; the fifth MBConv6 is connected with the sixth MBConv6; the sixth MBConv6 is connected with the Conv2 layer; the Conv2 layer is connected with the GAP layer; and the GAP layer is connected with the Sigmoid.

Further, the secondary network contains an input layer with the input size of (w, h, c), where w=224, h=224, and c=3. The input layer is connected with one Conv1 layer with the size of K3×3. Thereafter, the Conv1 layer is connected with one layer of MBConv1 with the size of K3×3. Thereafter, the one layer of MBConv1 is connected with two layers of MBConv6 with the size of K3×3. Thereafter, the two layers of MBConv6 are connected with two layers of MBConv6 with the size of K5×5. Thereafter, the two layers of MBConv6 are connected with three layers of MBConv6 with the size of K3×3. Thereafter, the three layers of MBConv6 are connected with three layers of MBConv6 with the size of K5×5. Thereafter, the three layers of MBConv6 are connected with four layers of MBConv6 with the size of K5×5. Thereafter, the four layers of MBConv6 are connected with one MBConv6 layer with the size of K3×3. Thereafter, the one MBConv6 layer is connected with one Conv2 layer with the size of K1×1. Thereafter, the one Conv2 layer is connected with the GAP layer. Thereafter, the GAP layer is connected with the Sigmoid.

The final output results in the present disclosure are the output results of the primary network and the secondary network, which includes the posterior echo being enhanced, and the posterior echo being unchanged, which are output by the primary network; the posterior echo being attenuated-sharp or the posterior echo being attenuated-blurred, which are output by the secondary network.

The present disclosure has the following advantages.

1) Compared with the traditional single image processing threshold measurement method, this method uses BrEff-net depth network to extract a plurality of depth features related to the posterior echo of the nodule. This method has higher accuracy than the previous method. In addition, this method adapts to ultrasound images of different qualities and sources through an image data enhancement method, and has less dependence on artificially set thresholds, which has wider applicability.

2) This method uses a two-stage deep learning network to further subdivide the posterior echo attenuation, which meets the clinical needs. The secondary network uses the lightweight network to reduce the computation. Compared with the traditional deep learning algorithm, the calculation efficiency and accuracy can be further improved. Compared with other methods based on machine learning, this method uses a large number of images and covers a variety of nodules for training, which also ensures that this method can make accurate measurements on different categories of nodules.

Embodiment 2

In order to implement the method corresponding to Embodiment 1 above, so as to achieve corresponding functions and technical effects, a system for classifying a breast ultrasound image is provided below, where the classifying system includes an acquiring module and a classifying module.

The acquiring module is configured to acquire a breast ultrasound image to be classified.

The classifying module is configured to input the breast ultrasound image to be classified into an image classification model to obtain a final classification result; where the final classification result is that a posterior echo is enhanced, the posterior echo is unchanged, the posterior echo is attenuated-sharp or the posterior echo is attenuated-blurred; the image classification model includes a primary classification network and a secondary classification network; the primary classification network is acquired by applying a primary training set to train a primary network; the secondary classification network is acquired by applying a secondary training set to train a secondary network; the primary network and the secondary network are both deep neural networks; the primary training set includes a breast ultrasound image and a corresponding primary classification result; the corresponding primary classification result is that the posterior echo is enhanced, the posterior echo is unchanged or the posterior echo is attenuated; the secondary training set includes a breast ultrasound image in which the primary classification result is that the posterior echo is attenuated and a corresponding secondary classification result; the secondary classification result is that the posterior echo is attenuated-sharp or the posterior echo is attenuated-blurred; the breast ultrasound image to be classified is input into the primary classification network to obtain the primary classification result; when the primary classification result is that the posterior echo is enhanced or the posterior echo is unchanged, the primary classification result is the final classification result; when the primary classification result is that the posterior echo is attenuated, the breast ultrasound image to be classified is input into the secondary classification network to obtain the secondary classification result, and the secondary classification result is deemed as the final classification result.

Embodiment 3

The embodiment of the present disclosure provides an electronic device, including a memory and a processor, where the memory is configured to store a computer program, and the processor runs the computer program to cause the electronic device to perform the method for classifying the breast ultrasound image according to Embodiment 1.

In some embodiments, the electronic device may be a server.

In addition, the embodiment of the present disclosure further provides a non-transitory computer-readable storage medium in which a computer program is stored, where the computer program, when executed by a processor, implements the method for classifying the breast ultrasound image according to Embodiment 1.

In this specification, various embodiments are described in a progressive way. The differences between each embodiment and other embodiments are highlighted, and the same and similar parts of various embodiments can be referred to each other. Since the system disclosed in the embodiment corresponds to the method disclosed in the embodiment, the system is described simply. Refer to the description of the method for the relevant points.

In the present disclosure, specific examples are applied to illustrate the principle and implementation of the present disclosure, and the explanations of the above embodiments are only used to help understand the method and core ideas of the present disclosure. At the same time, according to the idea of the present disclosure, there will be some changes in the specific implementation and application scope for those skilled in the art. To sum up, the contents of the specification should not be construed as limiting the present disclosure.

What is claimed is:

1. A method for classifying a breast ultrasound image, comprising:

acquiring a breast ultrasound image to be classified;

inputting the breast ultrasound image to be classified into an image classification model to obtain a final classification result; wherein the final classification result is that a posterior echo is enhanced, the posterior echo is unchanged, the posterior echo is attenuated-sharp or the posterior echo is attenuated-blurred;

the image classification model comprises a primary classification network and a secondary classification network;

the primary classification network is acquired by applying a primary training set to train a primary network;

the secondary classification network is acquired by applying a secondary training set to train a secondary network; the primary network and the secondary network are both deep neural networks;

the primary training set comprises a breast ultrasound image and a corresponding primary classification result; the corresponding primary classification result is that the posterior echo is enhanced, the posterior echo is unchanged or the posterior echo is attenuated;

the secondary training set comprises a breast ultrasound image in which the primary classification result is that the posterior echo is attenuated and a corresponding secondary classification result; the secondary classification result is that the posterior echo is attenuated-sharp or the posterior echo is attenuated-blurred;

the breast ultrasound image to be classified is input into the primary classification network to obtain the primary classification result; when the primary classification result is that the posterior echo is enhanced or the posterior echo is unchanged, the primary classification result is the final classification result; when the primary classification result is that the posterior echo is attenuated, the breast ultrasound image to be classified is input into the secondary classification network to obtain the secondary classification result, and the secondary classification result is deemed as the final classification result.

2. The method according to claim 1, wherein a construction process of the image classification model comprises:

acquiring a plurality of original breast ultrasound images and a region of interest of each original breast ultrasound image; wherein the plurality of original breast ultrasound images comprise a posterior echo enhanced image, a posterior echo unchanged image, a posterior echo attenuated-sharp image and a posterior echo attenuated-unsharp image;

determining a circumscribed matrix of the region of interest of each original breast ultrasound image, and determining a posterior echo prediction region according to the circumscribed matrix to obtain a labeled breast ultrasound image;

preprocessing the labeled breast ultrasound image to obtain a preprocessed breast ultrasound image; the preprocessing at least comprises two operations of flip transformation, random cropping, color dithering, translation transformation, scale transformation, contrast transformation, noise disturbance and rotation transformation;

with the preprocessed breast ultrasound image as an input and the primary classification result as an output, training the primary network to obtain the primary classification network;

with the classified breast ultrasound image as an input and the secondary classification result as an output, training the secondary network to obtain the secondary classification network; wherein the classified breast ultrasound image is an intermediate breast ultrasound image corresponding to the primary classification result that the posterior echo is attenuated; and the intermediate breast ultrasound image is the preprocessed breast ultrasound image.

3. The method according to claim 2, wherein the labeled breast ultrasound image is preprocessed, and prior to the preprocessing, the method further comprises: scaling the labeled breast ultrasound image to a predetermined pixel by applying an interpolation algorithm.

4. The method according to claim 3, wherein the interpolation algorithm is Lanczos interpolation algorithm.

5. The method according to claim 1, wherein a structure of the primary network comprises an input layer, a Conv1 layer, a Fused-MBConv1, a first Fused-MBConv4, a second Fused-MBConv4, an MBConv4, a first MBConv6, a second MBConv6, a Conv2 layer, a GAP layer and a Softmax;

the input layer is connected with the Conv1 layer; the Conv1 layer is connected with the Fused-MBConv1; the Fused-MBConv1 is connected with the first Fused-MBConv4; the first Fused-MBConv4 is connected with the second Fused-MBConv4; the second Fused-MB-Conv4 is connected with the MBConV4; the MBConv4 is connected with the first MBConv6; the first MBConv6 is connected with the second MBConv6; the second MBConv6 is connected with the Conv2 layer; the Conv2 layer is connected with the GAP layer; and the GAP layer is connected with the Softmax.

6. The method according to claim 1, wherein a structure of the secondary network comprises an input layer, a Conv1 layer, an MBConv1, a first MBConv6, a second MBConv6, a third MBConv6, a fourth MBConv6, a fifth MBConv6, a sixth MBConv6, a Conv2 layer, a GAP layer and a Sigmoid;

the input layer is connected with the Conv1 layer; the Conv1 layer is connected with MBConv1; the MBConv1 is connected with the first MBConv6; the first MBConv6 is connected with the second MBConv6; the second MBConv6 is connected with the third MBConv6; the third MBConv6 is connected with the fourth MBConv6; the fourth MBConv6 is connected with the fifth MBConv6; the fifth MBConv6 is connected with the sixth MBConv6; the sixth MBConv6 is connected with the Conv2 layer; the Conv2 layer is connected with the GAP layer; and the GAP layer is connected with the Sigmoid.

7. An electronic device, comprising a memory and a processor, wherein the memory is configured to store a computer program, and the processor runs the computer program to cause the electronic device to perform the method for classifying the breast ultrasound image according to claim 1.

8. The electronic device according to claim 7, wherein a construction process of the image classification model comprises:

acquiring a plurality of original breast ultrasound images and a region of interest of each original breast ultrasound image; wherein the plurality of original breast ultrasound images comprise a posterior echo enhanced image, a posterior echo unchanged image, a posterior echo attenuated-sharp image and a posterior echo attenuated-unsharp image;

determining a circumscribed matrix of the region of interest of each original breast ultrasound image, and determining a posterior echo prediction region according to the circumscribed matrix to obtain a labeled breast ultrasound image;

preprocessing the labeled breast ultrasound image to obtain a preprocessed breast ultrasound image; the preprocessing at least comprises two operations of flip transformation, random cropping, color dithering, translation transformation, scale transformation, contrast transformation, noise disturbance and rotation transformation;

with the preprocessed breast ultrasound image as an input and the primary classification result as an output, training the primary network to obtain the primary classification network;

with the classified breast ultrasound image as an input and the secondary classification result as an output, training the secondary network to obtain the secondary classification network; wherein the classified breast ultrasound image is an intermediate breast ultrasound image corresponding to the primary classification result that the posterior echo is attenuated; and the intermediate breast ultrasound image is the preprocessed breast ultrasound image.

9. The electronic device according to claim 8, wherein the labeled breast ultrasound image is preprocessed, and prior to the preprocessing, the method further comprises: scaling the labeled breast ultrasound image to a predetermined pixel by applying an interpolation algorithm.

10. The electronic device according to claim 9, wherein the interpolation algorithm is Lanczos interpolation algorithm.

11. The electronic device according to claim 7, wherein a structure of the primary network comprises an input layer, a Conv1 layer, a Fused-MBConv1, a first Fused-MBConv4, a second Fused-MBConv4, an MBConv4, a first MBConv6, a second MBConv6, a Conv2 layer, a GAP layer and a Softmax;

the input layer is connected with the Conv1 layer; the Conv1 layer is connected with the Fused-MBConv1; the Fused-MBConv1 is connected with the first Fused-MBConv4; the first Fused-MBConv4 is connected with the second Fused-MBConv4; the second Fused-MB-Conv4 is connected with the MBConV4; the MBConv4 is connected with the first MBConv6; the first MBConv6 is connected with the second MBConv6; the second MBConv6 is connected with the Conv2 layer;

the Conv2 layer is connected with the GAP layer; and the GAP layer is connected with the Softmax.

12. The electronic device according to claim 7, wherein a structure of the secondary network comprises an input layer, a Conv1 layer, an MBConv1, a first MBConv6, a second MBConv6, a third MBConv6, a fourth MBConv6, a fifth MBConv6, a sixth MBConv6, a Conv2 layer, a GAP layer and a Sigmoid;

the input layer is connected with the Conv1 layer; the Conv1 layer is connected with MBConv1; the MBConv1 is connected with the first MBConv6; the first MBConv6 is connected with the second MBConv6; the second MBConv6 is connected with the third MBConv6; the third MBConv6 is connected with the fourth MBConv6; the fourth MBConv6 is connected with the fifth MBConv6; the fifth MBConv6 is connected with the sixth MBConv6; the sixth MBConv6 is connected with the Conv2 layer; the Conv2 layer is connected with the GAP layer; and the GAP layer is connected with the Sigmoid.

13. A non-transitory computer-readable storage medium in which a computer program is stored, wherein the computer program, when executed by a processor, implements the method for classifying the breast ultrasound image according to claim 1.

14. The non-transitory computer-readable storage medium according to claim 13, wherein a construction process of the image classification model comprises:

acquiring a plurality of original breast ultrasound images and a region of interest of each original breast ultrasound image; wherein the plurality of original breast ultrasound images comprise a posterior echo enhanced image, a posterior echo unchanged image, a posterior echo attenuated-sharp image and a posterior echo attenuated-unsharp image;

determining a circumscribed matrix of the region of interest of each original breast ultrasound image, and determining a posterior echo prediction region according to the circumscribed matrix to obtain a labeled breast ultrasound image;

preprocessing the labeled breast ultrasound image to obtain a preprocessed breast ultrasound image; the preprocessing at least comprises two operations of flip transformation, random cropping, color dithering, translation transformation, scale transformation, contrast transformation, noise disturbance and rotation transformation;

with the preprocessed breast ultrasound image as an input and the primary classification result as an output, training the primary network to obtain the primary classification network;

with the classified breast ultrasound image as an input and the secondary classification result as an output, training the secondary network to obtain the secondary classification network; wherein the classified breast ultrasound image is an intermediate breast ultrasound image corresponding to the primary classification result that the posterior echo is attenuated; and the intermediate breast ultrasound image is the preprocessed breast ultrasound image.

15. The non-transitory computer-readable storage medium according to claim 14, wherein the labeled breast ultrasound image is preprocessed, and prior to the preprocessing, the method further comprises: scaling the labeled breast ultrasound image to a predetermined pixel by applying an interpolation algorithm.

16. The non-transitory computer-readable storage medium according to claim 15, wherein the interpolation algorithm is Lanczos interpolation algorithm.

17. The non-transitory computer-readable storage medium according to claim 13, wherein a structure of the primary network comprises an input layer, a Conv1 layer, a Fused-MBConv1, a first Fused-MBConv4, a second Fused-MBConv4, an MBConv4, a first MBConv6, a second MBConv6, a Conv2 layer, a GAP layer and a Softmax;

the input layer is connected with the Conv1 layer; the Conv1 layer is connected with the Fused-MBConv1; the Fused-MBConv1 is connected with the first Fused-MBConv4; the first Fused-MBConv4 is connected with the second Fused-MBConv4; the second Fused-MB-Conv4 is connected with the MBConV4; the MBConv4 is connected with the first MBConv6; the first MBConv6 is connected with the second MBConv6; the second MBConv6 is connected with the Conv2 layer; the Conv2 layer is connected with the GAP layer; and the GAP layer is connected with the Softmax.

18. The non-transitory computer-readable storage medium according to claim 13, wherein a structure of the secondary network comprises an input layer, a Conv1 layer, an MBConv1, a first MBConv6, a second MBConv6, a third MBConv6, a fourth MBConv6, a fifth MBConv6, a sixth MBConv6, a Conv2 layer, a GAP layer and a Sigmoid;

the input layer is connected with the Conv1 layer; the Conv1 layer is connected with MBConv1; the MBConv1 is connected with the first MBConv6; the first MBConv6 is connected with the second MBConv6; the second MBConv6 is connected with the third MBConv6; the third MBConv6 is connected with the fourth MBConv6; the fourth MBConv6 is connected with the fifth MBConv6; the fifth MBConv6 is connected with the sixth MBConv6; the sixth MBConv6 is connected with the Conv2 layer; the Conv2 layer is connected with the GAP layer; and the GAP layer is connected with the Sigmoid.

19. A system for classifying a breast ultrasound image, comprising:

an acquiring module, configured to acquire a breast ultrasound image to be classified;

a classifying module, configured to input the breast ultrasound image to be classified into an image classification model to obtain a final classification result; wherein the final classification result is that a posterior echo is enhanced, the posterior echo is unchanged, the posterior echo is attenuated-sharp or the posterior echo is attenuated-blurred;

the image classification model comprises a primary classification network and a secondary classification network;

the primary classification network is acquired by applying a primary training set to train a primary network;

the secondary classification network is acquired by applying a secondary training set to train a secondary network; the primary network and the secondary network are both deep neural networks;

the primary training set comprises a breast ultrasound image and a corresponding primary classification result; the corresponding primary classification result is that the posterior echo is enhanced, the posterior echo is unchanged or the posterior echo is attenuated;

the secondary training set comprises a breast ultrasound image in which the primary classification result is that the posterior echo is attenuated and a corresponding secondary classification result; the secondary classification result is that the posterior echo is attenuated-sharp or the posterior echo is attenuated-blurred; the breast ultrasound image to be classified is input into the primary classification network to obtain the primary classification result;

when the primary classification result is that the posterior echo is enhanced or the posterior echo is unchanged, the primary classification result is the final classification result;

when the primary classification result is that the posterior echo is attenuated, the breast ultrasound image to be classified is input into the secondary classification network to obtain the secondary classification result, and the secondary classification result is deemed as the final classification result.

* * * * *